United States Patent [19]

Richmond

[11] Patent Number: 5,445,623
[45] Date of Patent: Aug. 29, 1995

[54] DRIP CHAMBER WITH LUER FITTING

[76] Inventor: Frank M. Richmond, 205 A Grant St., Harvard, Ill. 60033

[21] Appl. No.: 98,499

[22] Filed: Jul. 28, 1993

[51] Int. Cl.$^6$ ............................................. A61M 5/00
[52] U.S. Cl. .................................... 604/251; 604/247
[58] Field of Search ............. 604/30, 89, 91, 246–247, 604/249, 251, 254, 256, 411, 414

[56] References Cited

U.S. PATENT DOCUMENTS

| | | | |
|---|---|---|---|
| 4,059,109 | 11/1977 | Tischlinger | 128/218 |
| 4,468,225 | 8/1984 | Tcheraz | 604/248 |
| 4,614,437 | 9/1986 | Buehler | 366/130 |
| 4,683,916 | 8/1987 | Raines | 137/854 |

FOREIGN PATENT DOCUMENTS 2666745  3/1992  France ................. 604/251

Primary Examiner—Corrine Maglione
Attorney, Agent, or Firm—John I. Rogitz

[57] ABSTRACT

A drip chamber has an open distal end and a luer fitting is positioned in the open distal end of the drip chamber to engage a complementary fitting associated with another IV component, e.g., an IV fluid bag. Thus, the drip chamber can be engaged with an IV bag without the use of "sharps".

23 Claims, 5 Drawing Sheets

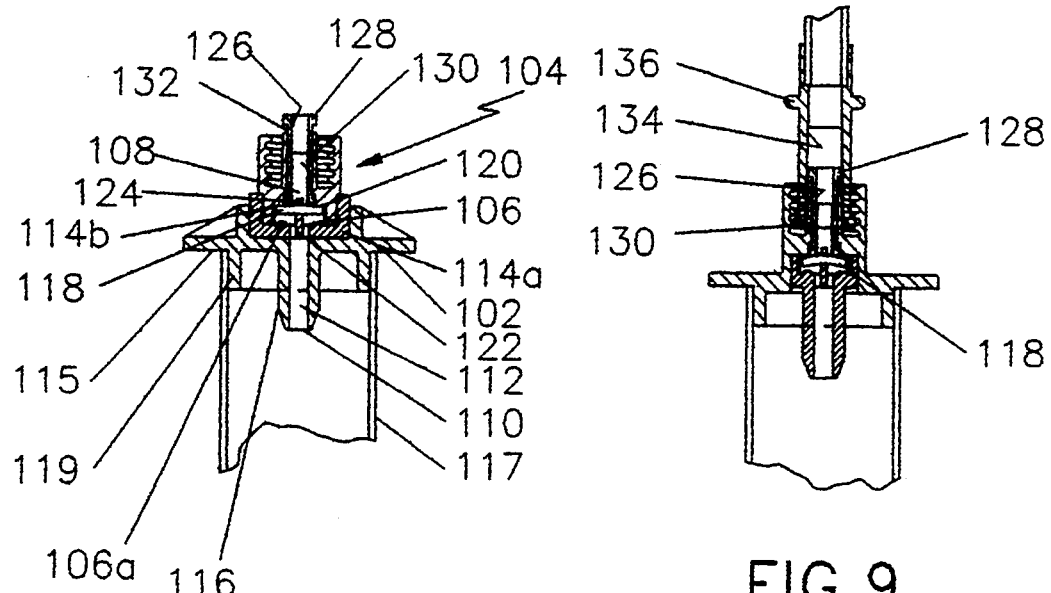
FIG.8.
FIG.9.
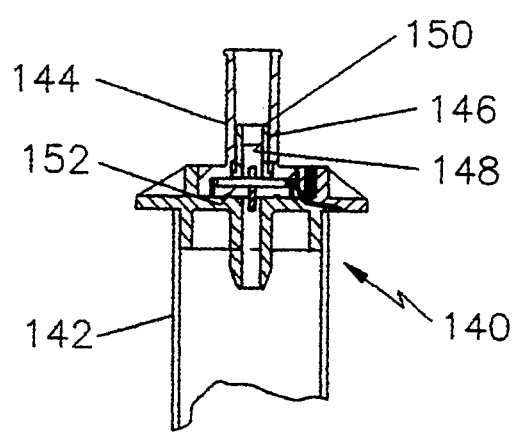
FIG.10.
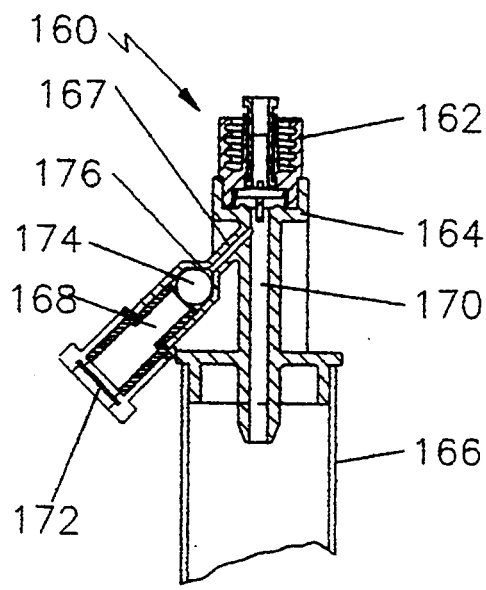
FIG.11.

DRIP CHAMBER WITH LUER FITTING

FIELD OF THE INVENTION

The present invention relates generally to IV set components, and more particularly to drip chambers and IV set valves.

BACKGROUND

One of the most widely used methods of medical therapy is the intravenous (IV) infusion of liquid medicaments and/or nutrients into the bloodstream of a patient. A familiar apparatus that is used in many IV infusion applications is an IV container, such as an IV bag or bottle, which contains the liquid to be infused into the patient.

When the IV container is a bag, a rigid, hollow, sharpened IV spike is pushed into the bag to establish a pathway for fluid communication through which the liquid can flow out of the bag. The spike, in turn, is connected to or formed integrally with an inlet port of a small, elongated, transparent hollow container familiarly referred to as a "drip chamber", with the fluid pathway of the spike in fluid communication with the inlet port of the drip chamber.

Additionally, an IV line is connected to an outlet port (which is located below the inlet port) of the drip chamber. Preferably, a roller clamp (or other suitable flow regulating device) is engaged with the IV line, and a medical technician can manipulate the roller clamp to squeeze the IV line and thereby regulate fluid flow through the IV line. To establish a path for fluid communication from the IV bag or bottle to the patient, a sharp needle is connected to the IV line to puncture the patient.

Usually, the bag or bottle is elevated above the patient to establish a positive pressure head to force the fluid that is within the bag or bottle through the drip chamber into the patient. Because the drip chamber is transparent, a medical technician can view the medicament as it passes (normally by dripping) through the drip chamber to aid the medical technician in establishing a predetermined flow rate of medicament into the patient as the medical technician adjusts the roller clamp on the IV line.

While effective as aids in establishing a predetermined fluid flow through the patient, existing drip chambers, as noted above, require the use of sharpened spikes to puncture the IV bag or bottle containing the liquid. This is undesirable, particularly in the era of AIDS, because spikes, like other sharps instruments, can inadvertently puncture the medical technician who is manipulating the spike and thereby potentially infect the technician with AIDS or other disease. Thus, as recognized by the present invention, it is desirable to avoid the use of sharp instruments whenever possible.

Further, it is desirable to connect and disconnect IV lines to the drip chamber without spillage of medicament. As recognized by the present invention, such reduction in spillage can be obtained through the use of reflex valves which are compatible with needleless drip chambers and other needleless IV components.

Accordingly, it is an object of the present invention to provide a drip chamber which does not require the use of "sharps" in infusing or extract fluid from the bag. Another object of the present invention to provide a drip chamber which is easy to use and cost-effective to manufacture. A further object of the present invention is to provide a valve apparatus in an IV drip chamber or other IV component for engaging a complementary fitting, without the need to use a sharp connector.

SUMMARY OF THE INVENTION

A drip chamber includes a container defining a hollow chamber, and the container has a proximal end and a distal end. Preferably, the proximal end of the container is engageable with an intravenous (IV) tube to establish a pathway for fluid communication between the IV tube and the chamber of the container. A fitting is attached to the container near the distal end of the container, and the fitting includes an annular element which has a dull distal end and a passageway in fluid communication with the chamber. As intended by the present invention, the element is positioned with the dull distal end of the element protruding away from the open distal end of the container.

In the presently preferred embodiment, the element is a male element, preferably a male luer fitting, and the drip chamber further includes an annular cap engaged with the male element in a surrounding relationship therewith. The cap has a threaded inner surface which faces the male element and which is spaced from the male element for threadably engaging a complementarily threaded surface.

If desired, the cap can be rotatably engaged with the male element. In this embodiment, the male element is formed with a collar and the cap is formed with a flange protruding inwardly from the threaded inner surface of the cap for abutting the collar and preventing the flange from moving distally past the collar. Furthermore, the flange of the cap has at least one opening formed therein, and the collar of the male element has a tapered surface for permitting the collar to move distally through the opening of the flange. Accordingly, the collar is substantially prevented from moving proximally through the opening. Alternatively, the cap can be fixedly attached to the male element.

To hold the fitting onto the container, the fitting includes a sleeve attached to the male element and engageable with the container.

In another embodiment, a valve is disposed in the passageway of the fitting to selectively permit fluid communication through the passageway. The valve has a closed configuration and an open configuration, and the valve is biased to the closed configuration and is moved to the open configuration when the fitting is operably engaged with a complementary fitting.

In accordance with the present invention, the valve includes a hollow body which defines a fluid passageway therethrough. A resilient valve disc is positioned in the fluid passageway of the body and is biased into a closed configuration, wherein the disc blocks fluid flow through the fluid passageway. Also, the disc is movable to an open configuration, wherein fluid flow is permitted through the fluid passageway.

Moreover, the valve includes a support element positioned on the valve body for supporting the valve disc at the center of the disc, and at least one protrusion is formed on the body for contacting the disc in the open configuration. Also, a retainer element is positioned in the valve on the opposite side of the disc from the support element, to hold the center of the disc against the support element. Importantly, a valve element is reciprocally disposed in the fluid passageway of the valve on the same side of the disc as the retainer element. The valve element is movable between a first position, wherein the valve element is distanced from the valve disc and at least a portion of the valve element protrudes distally beyond the dull distal end of the male element of the fitting, and a second position, wherein the valve element contacts the valve disc to move the disc into its open configuration, wherein the valve element is moved to its second position when the fitting is engaged with a complementary fitting.

In another aspect of the present invention, a device is disclosed for permitting visual monitoring of fluid flow from a fluid source having a luer fitting to an intravenous (IV) tube. The device includes a hollow transparent drip chamber which is engageable with the IV tube, and a luer fitting that is attached to the drip chamber and which is engageable with the luer fitting of the fluid source.

In yet another aspect of the present invention, a method is disclosed for establishing fluid communication between an intravenous (IV) tube and a fluid source having a fitting. The method of the present invention includes the steps of providing a drip chamber, and attaching a luer fitting to the drip chamber. Then, the drip chamber is engaged with the IV tube. Next, the luer fitting is engaged with the fitting of the fluid source, to thereby establish fluid communication between the fluid source and the IV tube.

In still another aspect of the present invention, a valve has a closed configuration and an open configuration, wherein the valve is biased to the closed configuration and is movable to the open configuration. The valve of the present invention includes a hollow body that defines a fluid passageway, and a resilient valve disc which is positioned in the fluid passageway of the body.

The valve disc is biased into a closed configuration, wherein the disc blocks fluid flow through the fluid passageway. Also, the disc is movable to an open configuration, wherein fluid flow is permitted through the fluid passageway.

A support element is positioned on the valve body for supporting the valve disc at the center of the disc, and at least one protrusion is formed on the body for contacting the disc in the open configuration. A retainer element is positioned in the valve on the opposite side of the disc from the support element, to hold the center of the disc against the support element, and a valve element is reciprocally disposed in the fluid passageway of the valve on the same side of the disc as the retainer element.

The valve element is movable between a first position, wherein the valve element is distanced from the valve disc and protrudes distally beyond the valve body, and a second position, wherein the valve element contacts the valve disc to move the disc into its open configuration. As intended by the present invention, the valve element includes a cylindrical outer surface and an engagement member protruding radially outwardly from the cylindrical outer surface for contacting an interior surface of a female luer fitting to move the valve element to its second position.

The details of the present invention, both as to its construction and operation, can best be understood in reference to the accompanying drawings, in which like numerals refer to like parts, and which:

BRIEF DESCRIPTION OF THE DRAWINGS

FIG. 8 is a cross-sectional view of the drip chamber embodiment shown in FIG. 7, with the components of the drip chamber shown in their operative relationships and the valve in the closed configuration, with portions cut away;

FIG. 9 is a cross-sectional view of the drip chamber embodiment shown in FIG. 7, with the components of the drip chamber shown in their operative relationships and the valve in the open configuration, with portions cut away;

FIG. 10 is a cross-sectional view of an alternate embodiment of the drip chamber with reflex valve, showing a female luer fitting, with portions cut away for clarity, with portions cut away;

FIG. 11 is a cross-sectional view of still another alternate embodiment of the drip chamber with reflex valve, showing a vented configuration of the drip chamber, with portions cut away for clarity;

DETAILED DESCRIPTION OF THE PREFERRED EMBODIMENT

Figure 1:
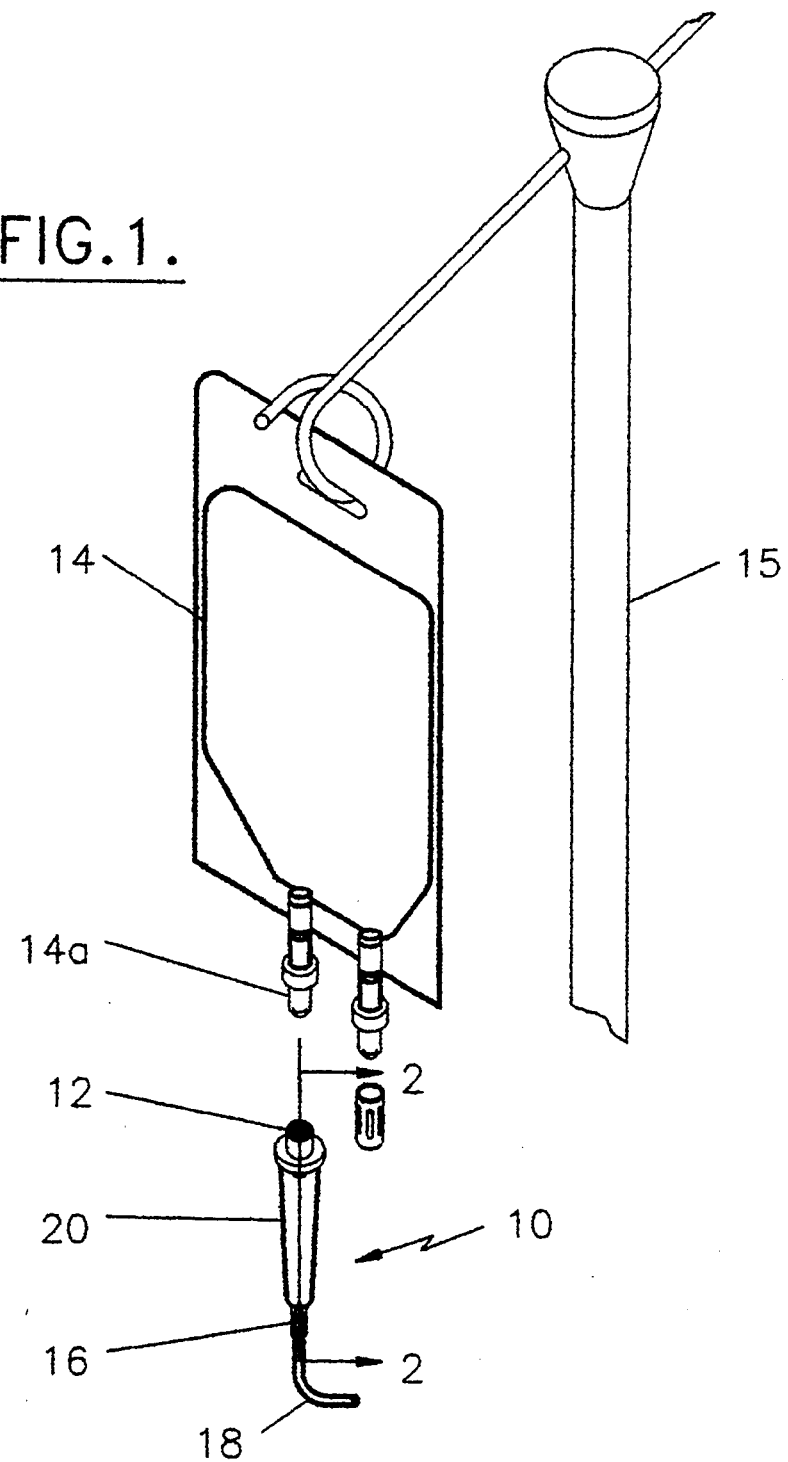
FIG. 1 is a perspective view of the drip chamber of the present invention, shown in an exploded relationship with an IV bag.

Referring initially to FIG. 1, a needleless plastic drip chamber is shown, generally designated 10. Preferably, the drip chamber 10 is made of polypropylene or polyethylene. As shown, the drip chamber 10 has a distal end 12 which can be operably engaged with a source 14 of fluid, such as the IV bag shown, and the IV bag can in turn be suspended from an IV pole 15. It is to be understood that the source 14 of fluid can be any container suitable for holding fluid medicaments, e.g., the source 14 can be an intravenous (IV) bag, vial, or bottle.

As further shown in FIG. 1, the drip chamber 10 has a proximal end 16 that can be engaged with an IV tube 18. Specifically, the IV tube 18 is advanced into the proximal end 16 of the drip chamber 10 and is held in the proximal end 16 by solvent bonding, rf sealing, or ultrasonic welding techniques.

Figures 2, 3, 4:
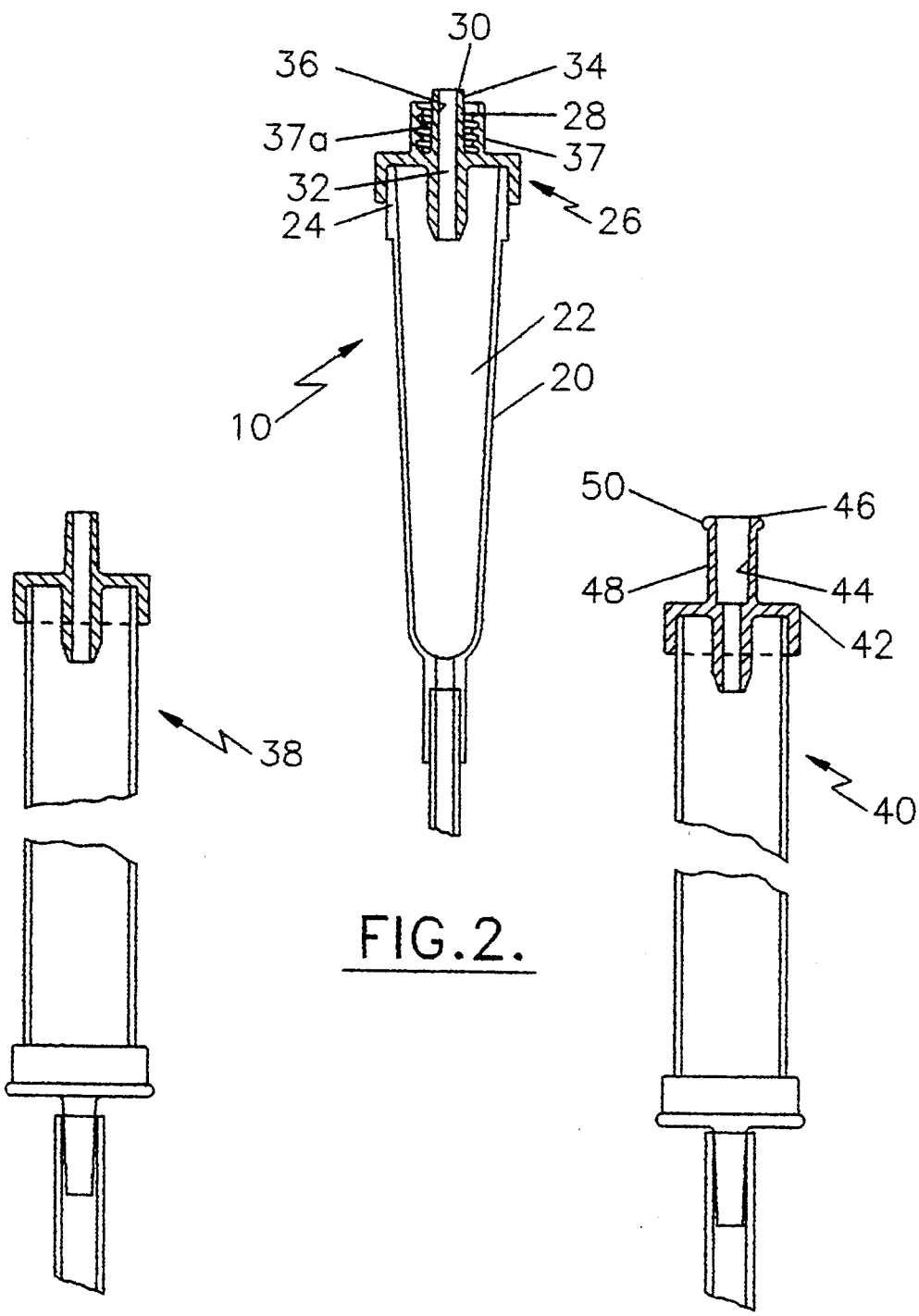
FIG. 2 is a cross-sectional view of the drip chamber shown in FIG. 1, as seen along the line 2—2 in FIG. 1.
FIG. 3 is a cross-sectional view of an alternate embodiment of the drip chamber of the present invention, as would be seen along the line 2—2 in FIG. 1, with portions cut away.
FIG. 4 is a cross-sectional view of another alternate embodiment of the drip chamber of the present invention, as would be seen along the line 2—2 in FIG. 1, with portions cut away.

Now referring to FIG. 2, the drip chamber 10 includes a hollow transparent glass or plastic container 20, and the container 20 defines a hollow chamber 22. As shown, the container 20 has an open distal end 24, and a needleless fitting, generally designated 26, is attached to the container 20 near the open distal end 24 of the container 20. In the embodiment shown, the fitting 26 is a male luer fitting for engaging a complementarily shaped female luer fitting 14a on the source 14 of fluid (FIG. 1).

More particularly, the fitting 26 includes an annular male element 28 that has a dull, i.e., non-sharp or blunt, distal end 30 and a passageway 32 in fluid communication with the chamber 22. As shown in FIG. 2, the male element 28 is positioned coaxially with the container 20, with the dull distal end 30 of the element 28 protruding away from the open distal end 24 of the container 20.

In further reference to FIG. 2, the male element 28 has an outside surface 34 which is frusto-conical in shape and an inside surface 36 which is cylindrical in shape. In other words, the outside surface 34 is slightly tapered radially inwardly toward the distal end 30 of the male element 28. A male luer locking ring 37 having a threaded surface 37a spaced from the male element 28 and facing the male element 28 is formed integrally with the male element 28 for threadably engaging the female luer fitting 14a (FIG. 1).

FIG. 3 shows an alternate embodiment of the drip chamber of the present invention, generally designated 38, which is in all essential respects identical to the drip chamber 10, except that the drip chamber 38 has no male luer locking ring.

FIG. 4 shows another alternate embodiment of the drip chamber of the present invention, generally designated 40, which is in all essential respects identical to the drip chamber 10, except that the drip chamber 40 has a needleless fitting 42 configured as a female luer fitting. Such an embodiment is used to engage a male luer fitting on a source of fluid (not shown). Accordingly, the female luer fitting 42 has a frusto-conical inside surface 44 which is slightly radially tapered outwardly toward a distal end 46 of the fitting 42, a cylindrical outside surface 48, and luer ears 50 formed near the distal end 46 which project radially outwardly from the outside surface 48 for engaging a male luer fitting (not shown in FIG. 4).

Figures 5, 6, 7:
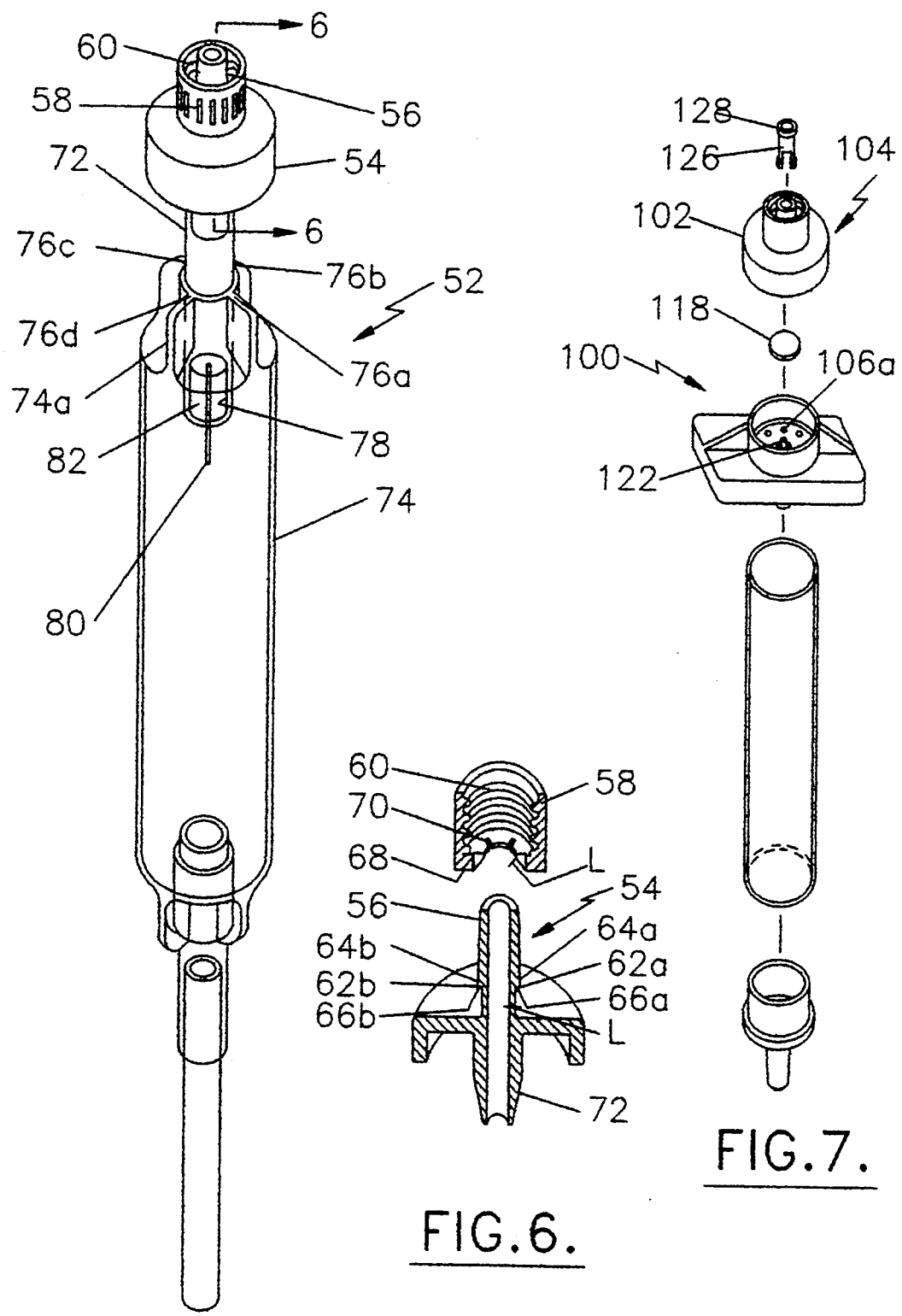
FIG. 5 is a perspective view of still another alternate embodiment of the drip chamber of the present invention, with a flow restrictor shown in phantom.
FIG. 6 is a cross-sectional view of the drip chamber shown in FIG. 5, as seen along the line 6—6 in FIG. 5, with portions cut away.
FIG. 7 is an exploded view of yet another alternate embodiment of the drip chamber of the present invention having a reflex valve.

FIGS. 5 and 6 show yet another alternate embodiment of the drip chamber of the present invention, generally designated 52. As shown, the drip chamber 52 has a fitting 54 having a male element 56 and a cap 58 rotatably engaged with the male element 56, and the cap 58 is formed with a threaded inner surface 60. Thus, the fitting 54 is configured as a male luer fitting. It is to be understood that the fitting 54 can be used in place of the fittings 26, 42 described above on the drip chambers 10, 40.

As best shown in FIG. 6, the male element 56 is formed with two or more collar elements 62a, 62b. As shown, each collar element 62a, 62b has a respective tapered surface 64a, 64b and a respective flat surface 66a, 66b. Each flat surface has a length L measured from the longitudinal axis of the male element 28 to the tip of the respective collar element 62a, 62b.

FIGS. 5 and 6 show that the annular, generally cylindrical cap 58 is rotatably engaged with the male element 56 in a surrounding relationship with the element 56, and the cap 58 is substantially coaxial with the male element 56. Importantly, the threaded inner surface 60 of the cap 58 faces the male element 56 and is spaced from the element 56 for threadably engaging a complementarily threaded surface of a female luer fitting.

In the embodiment shown in FIGS. 5 and 6, the cap 58 is rotatably engaged with the male element 56. In this embodiment, the cap 58 is formed with an annular flange 68 which protrudes inwardly from the threaded inner surface 60 of the cap 58 for abutting the collar elements 62a, 62b and preventing the flange 68 from moving distally past the collar elements 62a, 62b.

As best shown in FIG. 6, the flange 68 of the cap 58 has at least one, and preferably six (6), openings 70 formed in it. It can be appreciated in reference to FIG. 6 that the openings 70 are configured such that the collar elements 62a, 62b can move distally through the openings 70, upon proper alignment of the collar elements 62a, 62b with the openings 70, while substantially preventing the collar elements 62a, 62b from moving proximally through the openings 70.

More specifically, each opening 70 has a length L' measured from the longitudinal axis of the cap 58 to the respective end of the opening 70, and the lengths L' of the openings 70 are marginally less than the lengths L of the collar elements 62a, 62b. Consequently, the cap 58 can be pushed proximally onto the male element 56, and when the tapered surfaces 64a, 64b of the collar elements 62a, 62b are aligned with respective openings 70, the collar elements 62a, 62b can be squeezed through respective openings 70. Distal motion of the flange 68 past the collar elements 62a, 62b, however, is prevented because the flat surfaces 66a, 66b of the collar elements 62a, 62b cannot easily pass proximally through the openings 70. In other words, with the combination of structure described herein, the cap 58 can be snapped onto the male element 56 to hold the cap 58 in rotatable engagement with the male element 56.

As further shown in FIG. 5, the fitting 54 includes a rigid hollow tubular sleeve 72, and the sleeve 72 is attached to the male element 56 by solvent bonding, rf sealing, spin welding, or sonic welding. Alternatively, the sleeve 72 can be formed integrally with the male element 56. In either case, the sleeve 72 is engageable with a hollow drip chamber container 74 to hold the fitting 54 onto the container 74, thereby establishing the drip chamber 52. Specifically, the sleeve 72 can be solvent bonded to the container 74, or attached to the container 74 by any suitable means well-known in the art.

More specifically, FIG. 5 shows that the sleeve 72 by a well-known arrangement known as a four-way seal. With this arrangement, during manufacture, at least a portion 74a of the container 74 is heated, to make it malleable, and then heat-sealed or rf-sealed around the sleeve 72 of the fitting 54 at four points 76a, 76b, 76c, 76d to establish a fluid tight seal between the sleeve 72 and the container 74 at the points 76a, 76b, 76c, 76d.

Additionally, FIG. 5 shows that a flow restrictor 78 can be positioned in the sleeve 72. The flow restrictor 78 has a tube 80 which has a diameter sized such that fluid passes through the tube 80 at a predetermined rate, e.g., sixty (60) drips per minute or twenty (20) drips per minute. A resilient engagement element 82 is closely received in the sleeve 72, and the element 82 is held within the sleeve 72 by any suitable means well-known in the art, e.g. solvent bonding, rf sealing, or ultrasonic welding, to hold the flow restrictor 78 within the sleeve 72.

It is to be appreciated from the disclosure above that the fittings 26, 42, 54 are not sharp, i.e., they do not have any surfaces which can easily puncture a human body.

Now referring to FIGS. 7, 8, and 9, an alternate embodiment of the drip chamber of the present invention is shown, generally designated 100. The drip chamber 100 has a fitting 102 which is in all essential respects identical to the fitting 26 shown in FIGS. 1 and 2, except that a male reflex valve, generally designated 104, is positioned in the fitting 102 shown in FIGS. 7 and 8 for selectively permitting fluid communication through the fitting 102.

As shown best in FIG. 8, in one presently preferred embodiment the fitting 102 includes a rigid, preferably plastic (e.g., PVC) valve body 106 that has a fluid inlet 108, a fluid outlet 110, and a fluid passageway 112 formed in the valve body 106 between the inlet 108 and outlet 110. The valve body 106 can be a unitary structure, or be made of two or more pieces that are bonded together, as shown. For example, the inlet 108 can be formed from first pieces 114a, 114b, the outlet 110 can be formed from a second piece 116, and the pieces 114a, 114b, 116 can be bonded together by means well-known in the art, e.g., solvent bonding, ultrasonic sealing, or rf welding.

The second piece 116 can advantageously be formed with an annular flange 115 for providing a surface that can be manipulated to urge the fitting 102 into a container 117, or to engage the drip chamber 100 with an IV infusion pump (not shown). Then, a bonding collar 119 is bonded to the container 117.

In cross-reference to FIGS. 7, 8, and 9, the reflex valve 104 also includes a flexible resilient plastic or silicon rubber disc 118 that is disposed in the fluid passageway 112. Specifically, the periphery of the plastic disc 118 rests on a seating surface 120 of the valve body 106 to establish a fluid-tight seal between the disc 118 and seating surface 120, when the disc 118 is in the closed configuration shown in FIG. 8. It is to be understood that the valve disc 118 is biased to the closed configuration shown in FIG. 8, wherein no fluid communication is permitted through the valve 104 (and, hence, through the fitting 102). Cylindrical or pyramidal protrusions 106a are formed on the valve body 106 for preventing a vacuum lock from being established between the protrusions 106a and the valve disc 118. Alternatively, grooves (not shown) can be formed on the valve body 106 for preventing a vacuum lock from being established between the protrusions 106a and the valve disc 118.

FIG. 8 shows that a support element 122 is formed in the fluid passageway 112 and extends across the fluid passageway 112. As shown, the support element 122 supports the disc 118 in the center thereof. To this end, a slight depression may be formed in the center of the disc 118 to receive the support element 122 and thereby prevent side-to-side motion of the disc 118 relative to the support element 122. As further shown, the support element 122 is shaped as a cylinder, but it is to be understood that the support element 122 can have other suitable shapes, e.g., the support element 122 can have a triangular shape.

Additionally, a retainer element 124 is formed on the valve body 106 and extends across the fluid passageway 112. As shown in FIG. 7, the retainer element 124 is positioned on the valve body 106 on the opposite side of the valve disc 118 from the support element 122. Accordingly, the retainer element 124 holds the center of the valve disc 118 against the support element 122.

Still referring to FIGS. 7, 8, and 9, a hollow rigid valve element 126 is shown slidably disposed in the fluid passageway 112 for reciprocal movement therein. As shown, the valve element 126 has an engagement member, preferably an annular head 128, and a skirt 130 that depends from the head 128. As further shown, the skirt 130 includes a plurality of, preferably two, legs, and has a cylindrical outer surface 132. FIG. 8 best shows that when the disc 118 is in the closed configuration, the head 128 of the valve element 126 protrudes distally beyond the fitting 102.

In cross-reference to FIGS. 8 and 9, the head 128 of the valve element 126 protrudes radially outwardly from the cylindrical outer surface 132 of the skirt 130. Accordingly, as best shown in FIG. 9, the head 128 can contact a tapered interior surface 134 of a hollow female luer fitting 136 when the female luer fitting 136 is engaged with the male luer fitting 102. As the female luer fitting 136 is engaged with the male luer fitting 102, the valve element 126 is moved against the valve disc 118 to thereby deform the valve disc 118 into an open configuration, to permit fluid flow through the fluid passageway 112.

Stated differently, when the valve element 126 is forced against the valve disc 118 by the female luer fitting 136, the skirt 130 of the valve element 126 contacts the surface of the disc 118. This deforms the valve disc 118, causing the sealing surface of the disc 118 to be distanced from the seating surface 120 of the valve body 106, and thereby permitting fluid communication through the fluid passageway 112.

It is to be understood that when the female luer fitting 136 is disengaged from the male luer fitting 102, the resiliency of the valve disc 118 causes the disc 118 to resume its normally closed configuration, shown in FIG. 8.

Now referring to FIG. 10, a drip chamber generally designated 140 is shown which has a transparent hollow container 142 and a non-sharp fitting 144. As shown, the drip chamber 140 is substantially similar to the drip chamber 100 shown in FIGS. 7-9, except that the fitting 144 of the drip chamber 140 shown in Figure 9 is a female luer fitting. Also, the fitting 144 includes a valve element 146 which does not have an engagement surface which extends radially outwardly from a cylindrical skirt 148, in contrast to the valve element 126 shown in FIGS. 7-9. Instead, the valve element 146 has an engagement end 150 that is essentially a base of the cylindrical skirt 148. The end 150 is urged toward a valve disc 152 by a male luer fitting (not shown) during engagement of the male luer fitting with the female luer fitting 144 shown in Figure 10.

FIG. 11 shows a vented drip chamber, generally designated 160. As shown, the drip chamber 160 has a male luer fitting 162 that is in all essential respects identical to the fitting 126 shown in FIGS. 7-9, and which is connected by means well-known in the art to a vent fitting 164. In turn, the vent fitting 164 is connected to a hollow transparent container 166.

The purpose of the vent fitting 164 is to vent air from the container 166. Accordingly, the vent fitting 164 has a gas fitting 167 establishing a gas passageway 168 that is in fluid communication with the interior of the container 166 via a fluid passageway 170 that is formed in the vent fitting 164.

A hydrophobic membrane 172 is positioned athwart the gas passageway 168, and a ball 174 is positioned for reciprocating movement within the gas passageway 168. The ball 174 can contact a seat 176 that is formed in the gas fitting 167 when no air is present in the container 166, to block fluid flow through the gas passageway 168. On the other hand, gas within the container 166 will urge the ball 174 away from the seat 176 to permit the gas to pass out of the container 166 through the fluid passageway 170, gas passageway 168, and hydrophobic membrane 172.

Figure 12:
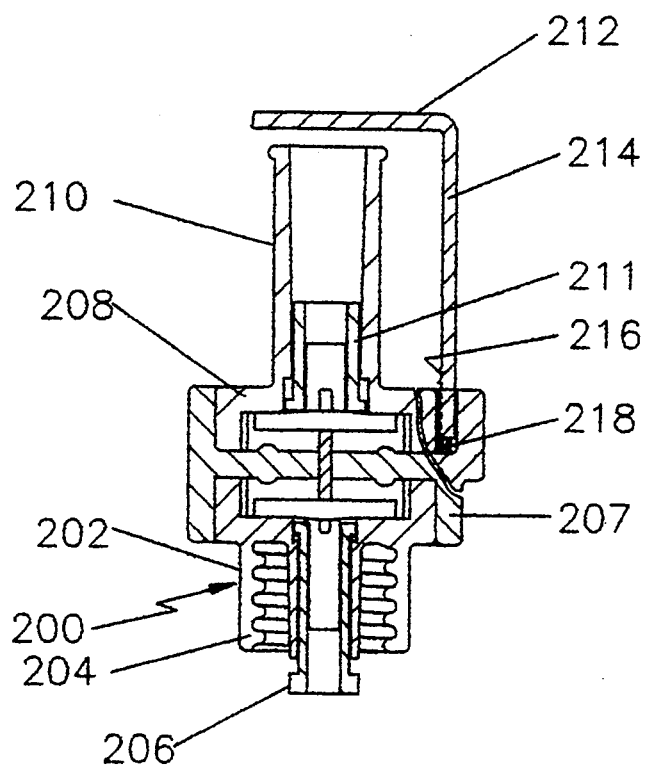
FIG. 12 is a cross-sectional view of another alternate embodiment of the reflex valve of the present invention, shown in a male-female adaptor configuration, with portions cut away.

Now referring to FIG. 12, a male-female reflex valve, generally designated 200, is shown. The valve 200 has a valve body 202 establishing a male luer fitting 204, and a male valve element 206 is positioned in the valve body 202. The valve body 202 is bonded to a support piece 207. Alternatively, the body 202 can be attached to the support piece 207 by ultrasonic welding or rf sealing.

As shown in FIG. 12, the valve 200 is in all essential respects identical to the valve 104 shown in FIGS. 7-9, except that the valve 200 shown in FIG. 12 is not positioned in a drip chamber fitting. Instead, the valve 200 can be used as a connector between two complementary luer fittings to selectively permit fluid communication through the valve 200.

Accordingly, in contrast to the piece 116 of the valve 104 shown in FIGS. 7-9, a piece 208 of the valve 200 corresponding to the piece 116 is configured as a female luer fitting 210, and is bonded to the support piece 207. Thus, it can be appreciated that the male luer fitting 204 can be engaged with a female luer fitting (not shown) which is associated with a first IV component, while the female luer fitting 210 is engaged with a male luer fitting (not shown) which is associated with a second IV component. Additionally, if desired, a female valve element 211 can be positioned within the female luer fitting 210, to selectively establish fluid communication between the two components only when both luer fittings are engaged with the valve 200.

If further desired, a tamper-resistant cap 212 can be engaged with the reflex valve 200. In one presently preferred embodiment, a skirt 214 of the cap 212 has a plurality of resilient ratchet threads 216. The ratchet threads 216 are configured generally as right triangles, as shown, and permit rotation of the cap 212 in the clockwise direction relative to the reflex valve 200 to thereby engage the cap 212 with the reflex valve 200. The threads 216 do not, however, permit easy rotation of the cap 212 in the counter clockwise direction. The threads 216 ratchetably engage blades 218 that are formed on the valve body 202. It is to be understood that the cap 212 can engage any appropriate surface of the valve body 202.

As can be appreciated by the skilled artisan, to disengage the cap 212 from the reflex valve 200, sufficient torque must be imparted to the cap 212 to strip to ratchet threads 216. Consequently, once the cap 212 has been removed from the reflex valve 200, it cannot be re-engaged with the reflex valve 200. Thus, a missing or stripped cap 212 indicates that the cap 212 has been tampered with. It is to be understood that if desired, a new cap (not shown) that is in all essential respects identical to the cap 212 can then be engaged with the reflex valve 200. If desired, the new cap can have a color which is different from the color of the cap 212.

Figure 13:
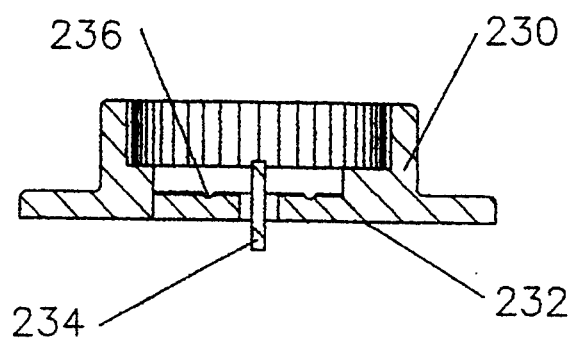
FIG. 13 is a cross-sectional view of a bag fitting of an alternate embodiment of the present invention.

FIG. 13 shows a needleless bag fitting 230 that can be bonded to the valve body 202 shown in FIG. 12 in place of the support piece 207 and female luer fitting 210. As shown, the bag fitting 230 has a flat surface 232 which can be bonded to the surface of a fluid container, e.g., an IV bag (not shown) in a so-called bellybutton arrangement. If desired, a protrusion 234 can be formed on the flat surface 232, and the protrusion 234 extends away from the surface 232. The protrusion 234 can accordingly urge aside a perforated portion of the IV bag to establish a path for fluid communication from the bag to the bag fitting 230. Also, the bag fitting 230 can have grooves 236 formed thereon to function analogously to the protrusions 106a shown in FIGS. 7-9, i.e., to prevent a vacuum lock from being established between the grooves 236 and a valve disc similar to the disc 118 shown in FIGS. 7-9.

While the particular drip chamber as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is:

1. A drip chamber for use with a source of fluid, comprising:
   a transparent container defining an elongated hollow chamber, the container having an open proximal end and a distal end; and
   a fitting attached to the container near the distal end of the container, the fitting including:
   an annular male element having a dull distal end and a passageway in fluid communication with the chamber, the element being positioned with the dull distal end of the element protruding away from the distal end of the container; and
   an annular cap engaged with the male element in a surrounding relationship therewith, the cap having a threaded inner surface facing the male element and spaced therefrom for threadably engaging a complementarily threaded surface associated with the source of fluid, wherein fluid from the source of fluid can flow through the chamber from the distal end of the container through the open proximal end thereof, to thereby permit the flow of the fluid from the distal end to the proximal end to be visually monitored.

2. The drip chamber of claim 1, wherein the cap is rotatably engaged with the male element.

3. The drip chamber of claim 2, wherein the male element is formed with a collar and the cap is formed with a flange protruding inwardly from the threaded inner surface of the cap for abutting the collar and preventing the flange from moving distally past the collar.

4. The drip chamber of claim 3, wherein the flange of the cap has at least one opening formed therein, and the collar of the male element has a tapered surface for permitting the collar to move distally through the opening of the flange, and for substantially preventing the collar from moving proximally through the opening.

5. The drip chamber of claim 3, wherein the fitting includes a sleeve attached to the male element and engageable with the container to hold the fitting onto the container.

6. The drip chamber of claim 3, wherein the fitting includes a sleeve formed integrally with the male element and engageable with the container to hold the fitting onto the container.

7. The drip chamber of claim 1, wherein the cap is fixedly attached to the male element.

8. The drip chamber of claim 1, wherein the fitting is a male luer fitting.

9. The drip chamber of claim 8, wherein the proximal end of the container is configured for engaging an intravenous (IV) tube to establish a pathway for fluid communication between the IV tube and the chamber of the container.

10. The drip chamber of claim 9, further comprising a valve disposed in the passageway of the annular element of the fitting to selectively permit fluid communication through the passageway.

11. The drip chamber of claim 10, wherein the valve has a closed configuration and an open configuration, and the valve is biased to the closed configuration and is moved to the open configuration when the fitting is operably engaged with a complementary fitting.

12. The drip chamber of claim 11, wherein the valve includes:
  a hollow body defining a fluid passageway therethrough; and
  a resilient valve disc positioned in the fluid passageway of the body and being biased into a closed configuration, wherein the disc blocks fluid flow through the fluid passageway, the disc being movable to an open configuration, wherein fluid flow is permitted through the fluid passageway.

13. The drip chamber of claim 12, wherein the valve further comprises:
  a support element positioned on the valve body for supporting the valve disc at the center of the disc;
  at least one protrusion formed on the body for contacting the disc in the open configuration;
  a retainer element positioned in the valve on the opposite side of the disc from the support element, to hold the center of the disc against the support element; and
  a valve element reciprocally disposed in the fluid passageway of the valve on the same side of the disc as the retainer element, the valve element being movable between a first position, wherein the valve element is distanced from the valve disc and at least a portion of the valve element protrudes distally beyond the dull distal end of the male element of the fitting, and a second position, wherein the valve element contacts the valve disc to move the disc into its open configuration, wherein the valve element is moved to its second position when the fitting is engaged with a complementary fitting.

14. The drip chamber of claim 13, wherein the valve element is a male valve element having a skirt and a head extending radially outwardly from the skirt for engaging a female luer fitting.

15. The drip chamber of claim 13, wherein the valve further comprises:
  a support element positioned on the valve body for supporting the valve disc at the center of the disc;
  at least one groove formed on the body;
  a retainer element positioned in the valve on the opposite side of the disc from the support element, to hold the center of the disc against the support element; and
  a valve element reciprocally disposed in the fluid passageway of the valve on the same side of the disc as the retainer element, the valve element being movable between a first position, wherein the valve element is distanced from the valve disc and at least a portion of the valve element protrudes distally beyond the dull distal end of the male element of the fitting, and a second position, wherein the valve element contacts the valve disc to move the disc into its open configuration, wherein the valve element is moved to its second position when the fitting is engaged with a complementary fitting.

16. A device for permitting visual monitoring of fluid flow from a fluid source having a luer fitting to an intravenous (IV) tube, comprising:
  a hollow transparent elongated drip chamber having a proximal end engageable with the IV tube, the drip chamber also having a distal end; and
  a male luer fitting attached to the distal end of the drip chamber and engageable with the luer fitting of the fluid source, the male luer fitting including a male element and an annular cap engaged with the male element in a surrounding relationship therewith, the cap having a threaded inner surface facing the male element and spaced therefrom for threadably engaging the luer fitting of the fluid source, wherein fluid from the fluid source flows through the drip chamber from the distal end of the drip chamber to the proximal end of the drip chamber.

17. The device of claim 16, wherein the luer fitting establishes a fluid passageway, and the device further comprises a valve disposed in the passageway of the luer fitting to selectively permit fluid communication through the passageway.

18. The device of claim 17, wherein the valve has a closed configuration and an open configuration, and the valve is biased to the closed configuration and is moved to the open configuration when the luer fitting of the device is operably engaged with the luer fitting of the fluid source.

19. The device of claim 18, wherein the valve includes:
  a hollow body defining a fluid passageway therethrough; and
  a resilient valve disc positioned in the fluid passageway of the body and being biased into a closed configuration, wherein the disc blocks fluid flow through the fluid passageway, the disc being movable to an open configuration, wherein fluid flow is permitted through the fluid passageway.

20. The device of claim 19, wherein the valve further comprises:
  a support element positioned on the valve body for supporting the valve disc at the center of the disc;
  at least one protrusion formed on the body for contacting the disc in the open configuration;
  a retainer element positioned in the valve on the opposite side of the disc from the support element, to hold the center of the disc against the support element; and
  a valve element reciprocally disposed in the fluid passageway of the valve on the same side of the disc as the retainer element, the valve element being movable between a first position, wherein the valve element is distanced from the valve disc and protrudes distally beyond a distal end of the luer fitting of the device, and a second position, wherein the valve element contacts the valve disc to move the disc into its open configuration, wherein the valve element is moved to its second position when the luer fitting of the device is engaged with the luer fitting of the fluid source.

21. The drip chamber of claim 20, wherein the valve element is a male valve element having a skirt and a head extending radially outwardly from the skirt for engaging a female luer fitting.

22. The device of claim 19, wherein the valve further comprises:
- a support element positioned on the valve body for supporting the valve disc at the center of the disc;
- at least one groove formed on the body;
- a retainer element positioned in the valve on the opposite side of the disc from the support element, to hold the center of the disc against the support element; and
- a valve element reciprocally disposed in the fluid passageway of the valve on the same side of the disc as the retainer element, the valve element being movable between a first position, wherein the valve element is distanced from the valve disc and protrudes distally beyond a distal end of the luer fitting of the device, and a second position, wherein the valve element contacts the valve disc to move the disc into its open configuration, wherein the valve element is moved to its second position when the luer fitting of the device is engaged with the luer fitting of the fluid source.

23. A method for establishing fluid communication to an intravenous (IV) tube from a fluid source having a fitting, comprising the steps of:
 (a) providing an elongated transparent drip chamber formed with a proximal end and a distal end;
 (b) attaching a male luer fitting to the distal end of the drip chamber, the male luer fitting including a male element and an annular cap engaged with male element in a surrounding relationship therewith, the cap having a threaded inner surface facing the male element and spaced therefrom for threadably engaging a complementarily threaded surface;
 (c) engaging the proximal end of the drip chamber with the IV tube; and
 (d) engaging the luer fitting with the fitting of the fluid source to thereby establish a pathway for fluid communication from the fluid source to the IV tube, wherein fluid flows through the drip chamber from the distal end of the drip chamber to the proximal end of the drip chamber to permit visual monitoring of the fluid as it flows through the chamber.

* * * * *